United States Patent [19]

Setcavage et al.

[11] Patent Number: 5,491,067
[45] Date of Patent: Feb. 13, 1996

[54] AGGLUTINATION REACTION AND SEPARATION VESSEL

[75] Inventors: Thomas M. Setcavage; Kathleen J. Reis, both of Milford; Donald M. Davies, Raritan; Edward J. Mazur, Montville, all of N.J.

[73] Assignee: Ortho Diagnostic Systems Inc., Raritan, N.J.

[21] Appl. No.: 93,106

[22] Filed: Jul. 16, 1993

Related U.S. Application Data

[63] Continuation of Ser. No. 92,157, Jul. 15, 1993, abandoned.

[51] Int. Cl.$^6$ .................. G01N 33/536; G01N 33/537; G01N 33/538; G01N 33/558
[52] U.S. Cl. .................. 435/7.25; 422/58; 422/59; 422/68.1; 422/73; 422/101; 435/287.2; 435/288.1; 436/165; 436/514; 436/518; 436/519; 436/520; 436/531; 436/533; 436/534; 436/536; 436/538; 436/541; 436/805; 436/809; 436/810; 436/824

[58] Field of Search ................. 422/58, 59, 68.1, 422/72, 73, 99, 101, 102; 435/7.25, 296; 436/165, 514, 518–520, 531–534, 536, 538, 541, 805, 809, 810, 824

[56] References Cited

U.S. PATENT DOCUMENTS

| | | | |
|---|---|---|---|
| 4,111,754 | 9/1978 | Park | 422/102 |
| 4,895,706 | 1/1990 | Root et al. | 422/102 |
| 4,948,564 | 8/1990 | Root et al. | 422/58 |
| 5,035,866 | 7/1991 | Wannlund | 422/52 |

OTHER PUBLICATIONS

Millipone Catalog (1991–1992), pp. 223 and 225.

*Primary Examiner*—David Saunders
*Assistant Examiner*—Christopher L. Chin

[57] ABSTRACT

A vessel for conducting blood cell agglutination assays is disclosed. A barrier retains reactants in an upper chamber during incubation, then, in response to a force, permits reagents to enter a lower chamber containing a matrix for separating agglutination.

11 Claims, 4 Drawing Sheets

5,491,067

AGGLUTINATION REACTION AND SEPARATION VESSEL

This application is a continuation of U.S. Ser. No. 08/092,157 filed Jul. 15, 1993, now abandoned.

BACKGROUND OF THE INVENTION

This invention relates to the field of agglutination assays, and particularly to vessels useful for conducting agglutination assays and separating agglutinates.

Blood group serology requires the determination of blood cell compatibility between a blood donor and patient recipient before a transfusion or organ transplant involving the patient. Blood cell compatibility is determined by the absence of immunological reaction between antibodies contained in the blood serum of a patient and antigens present on blood cells from the donor.

Many different blood group antigens are found on the surface of red blood cells of every individual. Blood grouping is generally the process of testing red cells to determine which antigens are present and which are absent. This is generally accomplished by using antibodies of known specificity.

For detecting antibodies in the serum or plasma of a patient, reagents containing blood cells having known antigens are mixed with a serum sample. The reactants are incubated for a period of time sufficient to permit agglutination of the red blood cells, which occurs when antibodies against those antigens are present. The mixture is then centrifuged, and if agglutinated blood cells are present, such agglutinates are clearly visible at the bottom of the reaction vessel, thus indicating the presence of antibodies in the sample directed against the known antigens on the red blood cells. If no antibodies are present in the sample directed against the known antigens on the red blood cells, agglutination does not occur, and this is indicated by the absence of agglutinated red cells after centrifugation.

Recently, systems have been developed in which the agglutination reaction is carried out in one portion of a vessel, and separation of agglutinated red cells is accomplished in another portion of the same vessel using a matrix which separates agglutinated cells from other components in the reagent/sample mixture. One such system is disclosed and described in U.S. patent application Nos. 08/063,350, and 08/112,402, which is a continuation of application No. 08/023,500, now abandoned, both of which applications are commonly owned by the owner of the subject application. The contents of each of these applications are hereby incorporated by reference herein. Agglutination reaction and separation vessels according to the present invention, and which are also useful in the inventions disclosed in the aforementioned applications, are manufactured and sold by Ortho Diagnostic Systems Inc., Raritan, N.J., under the trademark BIOVUE™. Such reaction vessels are in the form of a column having an upper chamber and a lower chamber wherein the upper chamber is of a wider diameter than the lower chamber. The lower chamber contains a matrix for separating agglutinated cells from non-agglutinated cells. The diameter of the lower chamber is narrow enough such that when reagents and samples are added to the upper chamber, typically using a pipette, the reagents and samples remain in the upper chamber, and do not enter into the lower chamber, unless an additional force is applied.

An indirect antiglobulin test, known as the Coombs test, is a blood test used to determine whether there are IgG antibodies in a patient's serum to specified antigens on the surface of red blood cells. In the Coombs test, serum is incubated in the presence of reagent red cells to allow the antibodies to bind to antigens on the surface of the red cells. These IgG antibodies most often do not, by themselves, agglutinate the red cells, or only agglutinate them insufficiently to be detected visually by conventional techniques. Addition of a second antibody directed to human IgG is usually necessary to facilitate visible agglutination.

In red cell typing, a blood test used to determine whether certain antigens are present on the surface of red blood cells, the red cells being analyzed are added to the upper chamber followed by application of centrifugal force which moves them into the lower chamber containing antibodies to particular red cell antigens and the separation matrix. If the red cells have the antigen(s) on their surface to combine with the specific antibodies in the lower chamber, agglutinates will form and be separated by the matrix.

In other types of blood assays, such as reverse typing where directly agglutinating antibodies for red cell antigens in a patient's serum are being assayed, a patient's serum and reagent red blood cells with known antigens on their surface are added to the upper chamber and centrifugal force is applied to move the reactants into a lower chamber which contains a liquid medium and separation matrix but no antibody. In this assay the presence of directly agglutinating antibody in the patient's serum would produce agglutinates which would be separated by the matrix.

In another type of blood assay, reagent antibody with a known specificity for a red cell antigen would be deposited into the upper chamber, together with patient's red cells. If the reagent antibody is a directly agglutinating antibody, centrifugal force would be applied without prior incubation and the contents would be forced into the lower chamber containing separation matrix in aqueous solution. Agglutinates would then be separated by the matrix. Alternatively, patient's red cells are deposited into the upper chamber and IgG reagent antibody with known specificity is added, followed by incubation to allow the antibody to attach to presumptive antigens on the surface of the red cells. After incubation, centrifugal force is applied to move the reactants into the lower chamber which contains separation matrix and anti-IgG antibodies specific for the IgG reagent antibody used to incubate reed cells in the upper chamber. If the reagent antibody is present on the surface of the patient's cells, the anti-IgG antibody in the lower chamber would facilitate the formation of agglutinates which would be separated by the matrix.

After the sample and reagents have been allowed to incubate for a sufficient period of time to permit either direct agglutination, as in the case of a red cell typing test, an antibody-antigen reaction, as in the case of a Coombs test, the reaction vessel is centrifuged so that the reactants are expelled into the lower portion of the column and onto the separation matrix. As a result of the centrifugation, unagglutinated materials migrate down through the separation matrix while agglutinated cells remain on top of the separation matrix or distributed within the matrix depending on the degree of agglutination. Stronger agglutination reactions result in the cells remaining towards the upper portion of the separation matrix while weaker agglutination reactions result in distribution of agglutinates at various distances from the top of the matrix.

Retention of the sample and reagents in the upper portion of the column during the incubation phase is the result of surface tension across the top margin of the lower portion of the column where the diameter is reduced relative to the upper portion. Two potential sources of error in conducting an assay using this column have been identified. First, if reagents and sample are pipetted directly down the center of the reaction chamber with excessive force, the reactants may be deposited directly to the top of the separation matrix in the lower chamber and not retained in the upper chamber during the incubation phase. Thus, the reactants will begin to enter the separation matrix prior to the completion of agglutination. Second, there is potential that the diluent or solution which contains the separation matrix may enter the upper chamber. This can occur through splashing or other disturbance, for example, during shipping and handling of the vessels. In some cases where the solution or diluent containing the separation matrix also contains antibodies or other reagents which directly affect the result of a test, such splashing can result in cross-contamination of columns with certain reagents from other columns. This may occur when the user inserts a pipette tip into the reaction chamber, contaminating the tip with splashed reagent, which may then be transferred to another vessel by the pipette. This may lead to false results in the agglutination assay.

Thus, it is an object of the present invention to provide an improved mechanism for maintaining separation of sample and reagents during the incubation phase of an agglutination assay. It is a further object of the invention to provide means for preventing displacement of materials contained in the lower portion of the column.

SUMMARY OF THE INVENTION

The present invention provides an improved vessel for conducting an agglutination reaction and separating agglutinates. The vessel comprises an upper chamber which holds the reactants, a lower chamber in which agglutinates are separated, and a barrier means separating the chambers, which is capable of retaining reactants in the upper chamber prior to introduction of contents of the upper chamber to the separation matrix, and permitting the contents of the upper chamber to pass from the upper chamber to the lower chamber when a force is applied to the barrier. In a preferred embodiment, the barrier comprises a constricted passageway between the upper and lower chambers.

DETAILED DESCRIPTION OF THE INVENTION

In accordance with the present invention, vessels for conducting agglutination reactions and separating agglutinates will be described in terms of various embodiments. Certain embodiments of the invention may be clearly understood through the description of agglutination reaction and separation vessels manufactured and sold in cassette form by Ortho Diagnostic Systems Inc., Raritan, N.J., under the trademark BIOVUE™.

Vessels of the present invention may be manufactured from any suitable material which will not interfere with the agglutination reaction or separation, an visualization of results, such as glass or various plastics. In a preferred embodiment, the vessels are made from polypropylene.

Figure 6:
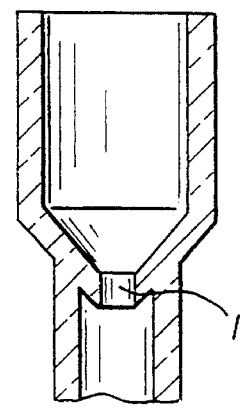
FIG. 6 shows the upper chamber of a reaction vessel constructed with a narrow aperture.
Figure 7:
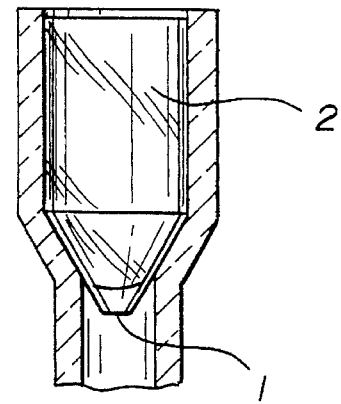
FIG. 7 shows an insert having an extended portion with an aperture disposed in the lower chamber.
Figure 8:
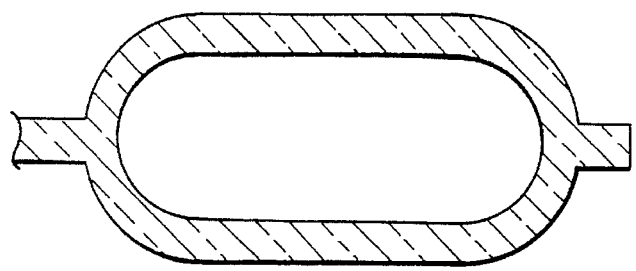
FIG. 8 is cross-sectional view along line 8—8 of FIG. 3.

The upper chamber of the vessel may be any shape and dimension useful for holding the reagents and sample while incubation is carried out. Typically, the upper chamber is cylindrical in the upper most portion. The barrier between the upper and lower chambers usually defines the lower boundary of the upper chamber and the upper boundary of the lower chamber. In a preferred embodiment, the barrier which forms the lower portion of the upper chamber is conical, with the apex extending toward or into the lower chamber, as shown in any of FIGS. 1, 5, 6, 7. A portion of the barrier is constructed to retain the reagents and sample of the upper chamber during incubation under normal gravity and atmospheric pressure conditions, while permitting fluid to flow from the first chamber to the second chamber when a force such as increased pressure or centrifugal force is applied. This may be accomplished by various means such as a small aperture, membrane, a plug, a constriction, or screen. In a preferred embodiment, the barrier comprises an aperture having a diameter small enough to prevent passage of fluid from the first chamber to the second chamber under normal gravity or atmospheric pressure, while permitting fluid to flow under increased pressure. The aperture 1 is located at the apex of the conical portion of the upper chamber, either in an insert 2, as shown in FIGS. 1, 5, or 7, or integrally formed in the upper chamber as shown in FIG. 6.

The aperture may be of any diameter which is small enough such that surface tension of the fluid in the upper chamber will prevent flow from the upper chamber to the lower chamber under normal gravity or atmospheric pressure, while permitting surface tension to be overcome and, thus, facilitating passage of contents from the upper chamber to the lower chamber under increased pressure or gravity forces. The aperture diameter may be altered according the magnitude of the force used, i.e. smaller diameter when greater force is applied and larger diameter when a lesser force is applied. The diameter may also be altered to accommodate different sized particles in the reagents. In a preferred embodiment, the diameter of the aperture is in the range of about 0.010 to 0.050 inch. In a particularly preferred embodiment, the diameter of the aperture is 0.020 inch.

Figure 1:
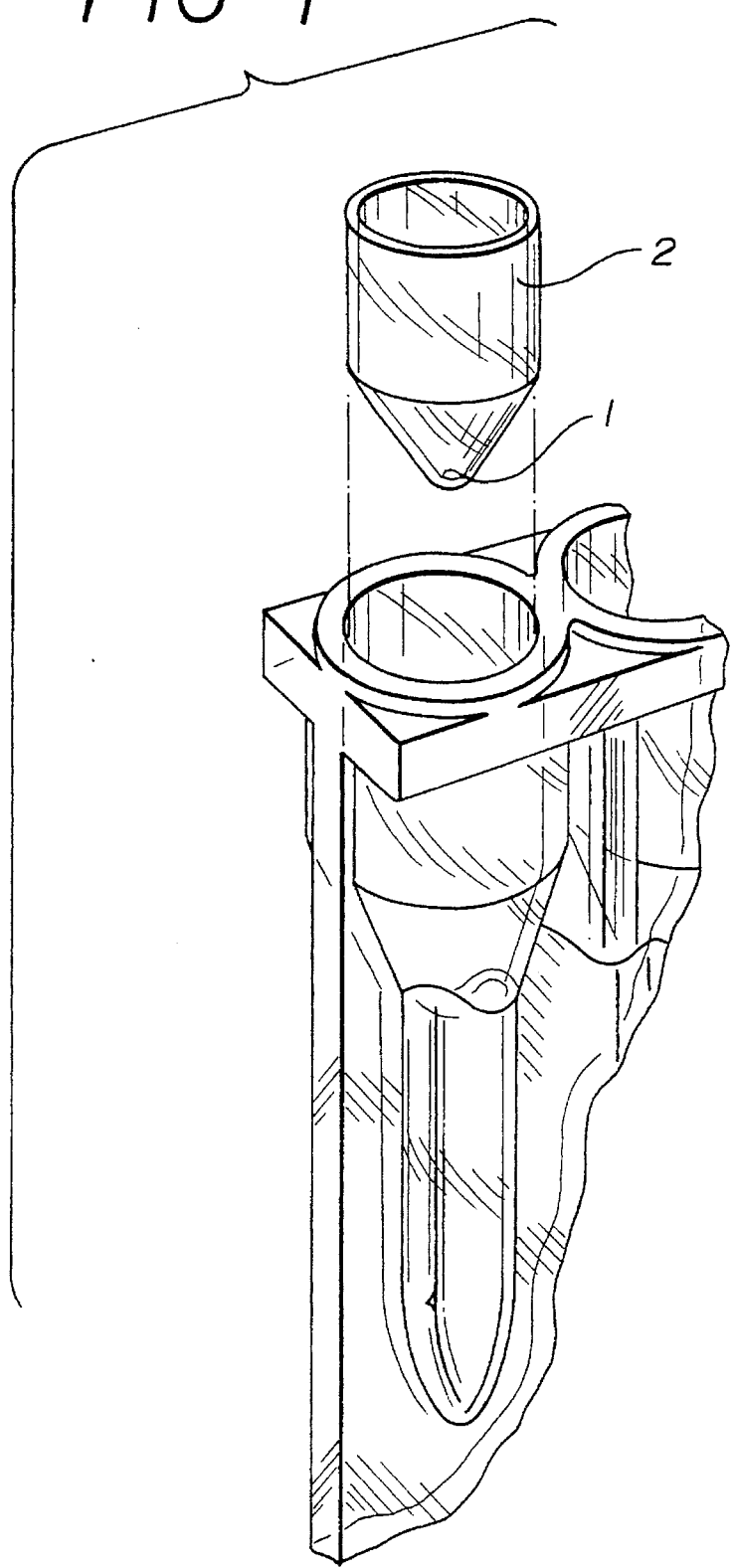
FIG. 1 shows a reaction and separation vessel with an insert having a narrow aperture placed in the upper reaction chamber.
Figure 2:
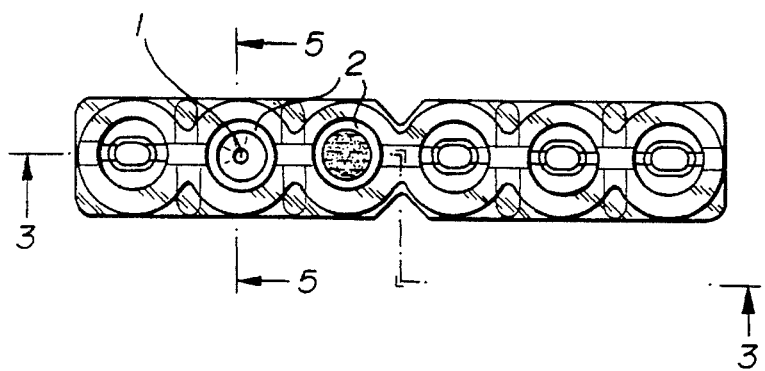
FIG. 2 is a top view of a cassette of six reaction vessels showing four vessels with no insert and one vessel (second from left) containing an insert as shown in FIG. 1, and one vessel (third from left) showing a vessel containing reactants.
Figure 3:
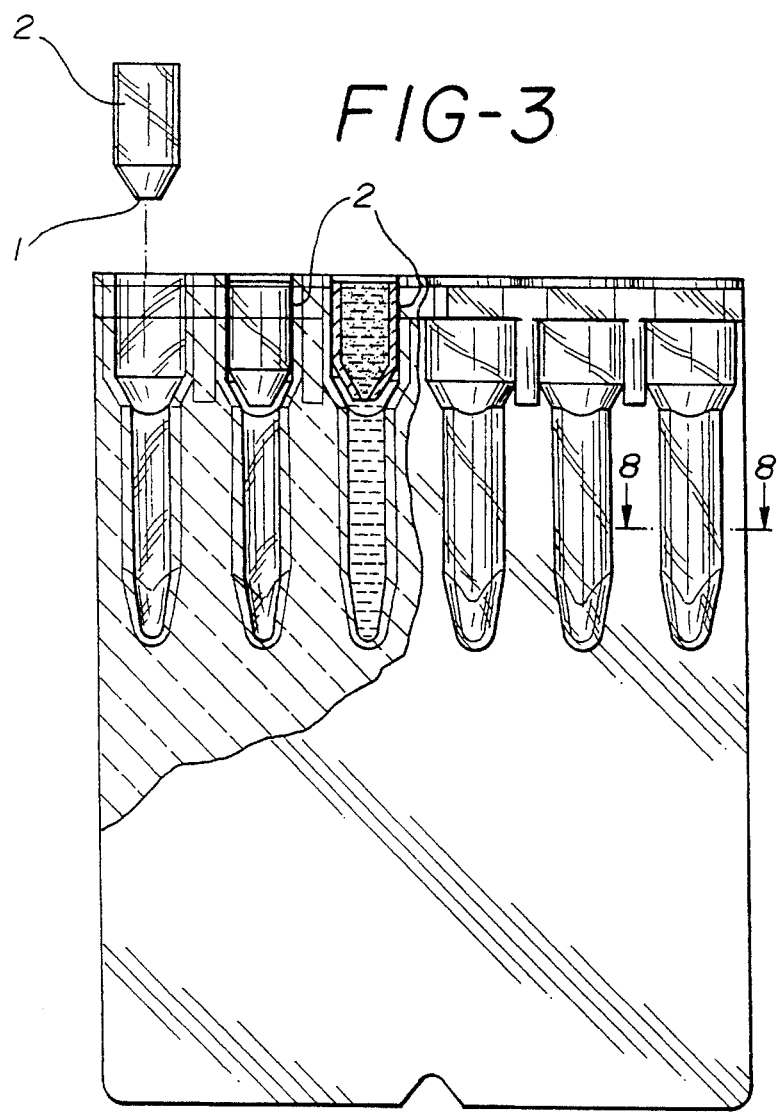
FIG. 3 is a cross-sectional view of a cassette of reaction vessels along the line 3—3 of FIG. 2.
Figure 4:
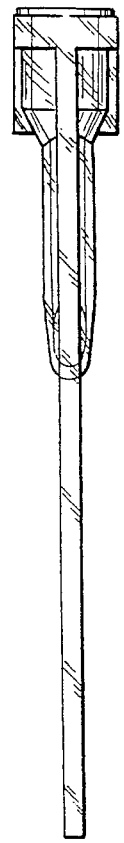
FIG. 4 is a side view of a cassette of reaction vessels.
Figure 5:
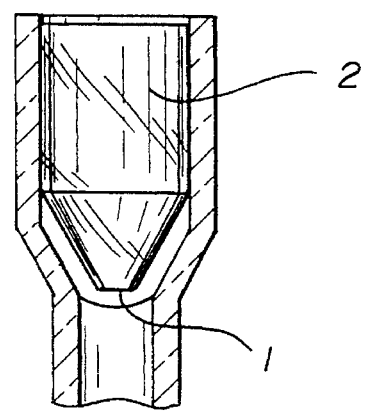
FIG. 5 is a cross-sectional view along the line 5—5 of FIG. 2, showing an insert with a narrow aperture inside the upper chamber of a reaction vessel.

Commonly available vessels sold in cassette form under the trademark BIOVUE™ have been adapted by placing in the upper portion an insert which is cylindrical in its upper portion and conical in its lower portion and which has an aperture at the apex of the conical portion as shown in FIGS. 1 and 5. In an alternative embodiment, the insert has a neck, or extended portion, which extends to and contacts with the upper margin of the lower chamber as shown in FIG. 7.

The lower chamber of the vessel may be of any shape and dimension useful for conducting separation of agglutinates from non-agglutinates. In one embodiment, the lower chamber may be cylindrical in cross-section. In another embodiment, the lower chamber may be elliptical or may be oval with substantially parallel sides in cross-section. The lower chamber generally contains a matrix for separating agglutinates from non-agglutinates in the reaction mixture. Such a matrix may be comprised of any suitable material for separating agglutinates such as glass beads, polymer beads, filter paper, gel filtration media, sintered glass, plastics.

When a vessel of the present invention is used to accomplish an agglutination reaction and separation, reagents and sample are added to the upper chamber for incubation. The barrier retains the sample and reagents in the upper chamber while the incubation occurs. In a preferred embodiment, where the barrier has an aperture, the diameter of the aperture is small enough that surface tension of the liquid and sample across the aperture will retain the contents in the upper chamber under normal gravity and atmospheric pressure. After sufficient incubation time, a force is applied by any of various means, such as by centrifugation, pressure, or suction, against the barrier in a direction substantially along the axis from the upper chamber to the lower chamber. The force must be sufficient to overcome the barrier and allow passage of the contents of the upper chamber into the lower chamber. In a preferred embodiment, where the barrier comprises an aperture, surface tension is overcome by the force, and the contents flow from the upper chamber into the lower chamber to the separation matrix.

In the Biovue™ system, incubation of 10 µl reagent red cell in 40 µl patient's serum, together with 40 µl of low ionic strength solution occurs in the upper chamber for 10 minutes to allow presumptive patient's IgG antibody to bind to red cell surface antigen(s). These assay components are added separately and it is important that they remain in the upper chamber so that they can mix, providing a constant ratio of low ionic strength solution to red cells to serum from assay to assay. The barrier serves to facilitate this under normal gravitational force and pressure. It also serves to reduce the chance of any of the assay components being forced into the lower chamber during sample addition. The barrier also enables the assay components to remain in the upper chamber throughout the incubation period.

The barrier is also important to prevent premature binding of the anti-human IgG antibodies to the presumptive anti-red cell antibodies in the patient serum before they have bound to red cells, reducing the chance of agglutination ultimately taking place in the lower chamber. After incubation, centrifugal force is applied to move the contents of the upper chamber through the barrier into the lower chamber which contains anti-human IgG which binds to the patient's IgG on the surface of the reagent red cells causing agglutinates to form which do not pass through the matrix to the bottom of the lower chamber.

EXAMPLE 1

BIOVUE™ columns with inserts were compared to columns without inserts to determine the efficacy of each configuration for maintaining the air space that separates the reactants from the separation matrix during the incubation period. Inserts having an aperture of 0.040 inch were used. 40 microliters of buffer solution were added to each of the 840 columns tested. A manual pipette held at approximately a 45 degree angle from the vertical axis of the column was used to deliver the 40 microliters. The columns were then observed to determine whether the air space beneath the reaction chamber was maintained. The number of "breakthroughs" is given in Table 1.

TABLE 1

|  | Number of Tests | Number of Breakthroughs | Percentage of Breakthroughs |
|---|---|---|---|
| Columns with Inserts | 840 | 0 | 0% |
| Columns Without Inserts | 840 | 231 | 27.5% |

EXAMPLE 2

Reagents were also added to columns (with and without inserts) and incubated for 10 minutes at 37° C. 40 microliters of buffer, 40 microliters of serum, and 10 microliters of red cell suspensions were added to each of the 480 columns tested. A pipette held at approximately a 45 degree angle was used to deliver the reactants. After the incubation period, the columns were inspected to determine whether the air space beneath the reaction chamber was maintained. The frequency of "break throughs" is given in Table 2.

TABLE 2

|  | Number of Tests | Number of Breakthroughs | Percentage of Breakthroughs |
|---|---|---|---|
| Columns with Inserts | 480 | 0 | 0% |
| Columns Without Inserts | 480 | 16 | 3.3% |

EXAMPLE 3

Columns were filled with 40 microliters of buffer using an automatic pipette held at about a 45 degree angle. Automatic pipettes typically deliver with more force than do manually operated models. Observations were made after filling, to determine if the air space beneath the reaction chamber was maintained. Results in columns with and without inserts are given in Table 3.

TABLE 3

|  | Number of Tests | Number of Breakthroughs | Percentage of Breakthroughs |
|---|---|---|---|
| Columns with Inserts | 240 | 0 | 0% |
| Columns Without Inserts | 240 | 103 | 43% |

EXAMPLE 4

240 columns were filled with 40 microliters of buffer using a single pipette held vertically. By holding the pipette vertically, the fluid is forced against the aperture with greater pressure and thus is more likely to break the air space separating the reaction chamber from the separation chamber. The results of this experiment are given in Table 4.

TABLE 4

|  | Number of Tests | Number of Breakthroughs | Percentage of Breakthroughs |
| --- | --- | --- | --- |
| Columns with Inserts | 240 | 0 | 0% |
| Columns Without Inserts | 240 | 144 | 60% |

EXAMPLE 5

The reaction chambers of 240 columns were also filled with 40 microliters of buffer using an automatic pipette held vertically, which is more likely to cause breaching of the air space beneath than when the automatic pipette is held at an angle. The results of these tests using columns with inserts and columns without inserts are given in Table 5.

TABLE 5

|  | Number of Tests | Number of Breakthroughs | Percentage of Breakthroughs |
| --- | --- | --- | --- |
| Columns with Inserts | 240 | 0 | 0% |
| Columns Without Inserts | 240 | 204 | 85% |

In addition to maintaining the air space between the reaction chamber and the separation matrix during the incubation phase of the test, the invention functions also as a means to prevent splashing that may occur during shipping and handling in which part of the contents of the lower separation chamber may splash up into the upper reaction chamber. To test the efficacy of splash prevention, cassettes with and without inserts were shipped from New Jersey to California and back. Shipping was by way of air and land included loading, unloading, and delivery to the laboratory. The method used was common for this product line. After the return shipment, the cassettes were examined for the presence of splashed liquid in the reaction chambers. Results are given in Table 6.

TABLE 6

|  | Number of Tests | Number of Columns with Splashes | Percentage of Columns with Splashes |
| --- | --- | --- | --- |
| Columns with Inserts | 816 | 30 | 3.7% |
| Columns Without Inserts | 768 | 571 | 74.3% |

EXAMPLE 7

An additional shipping study was conducted to test for splash reduction with inserts having apertures of diminishing size. The openings between the reaction chamber and the separation matrix were 0.025, 0.020, and 0.015 inches in diameter. 600 columns were fitted with each of these inserts. The control had no inserts. The cassettes were packaged and subjected to an in-house surrogate shipping study in which the box was dropped 10 times from a height of 3 feet. The angle of the box was controlled so that the container dropped on all 6 of its flat surfaces as well as on 1 corner and on 3 edges. This standardized test represents the words case for shipping and handling. The results given in Table 7 show the inverse relationship between aperture size and splash reduction.

TABLE 7

|  | Number of Tests | Number of Columns with Splashes | Percentage of Columns with Splashes |
| --- | --- | --- | --- |
| Columns with .015 Inserts | 600 | 75 | 13% |
| Columns with .020 Inserts | 600 | 120 | 20% |
| Columns with .025 Inserts | 600 | 132 | 22% |
| Columns without Inserts | 600 | 600 | 100% |

EXAMPLE 8

Figure 9:
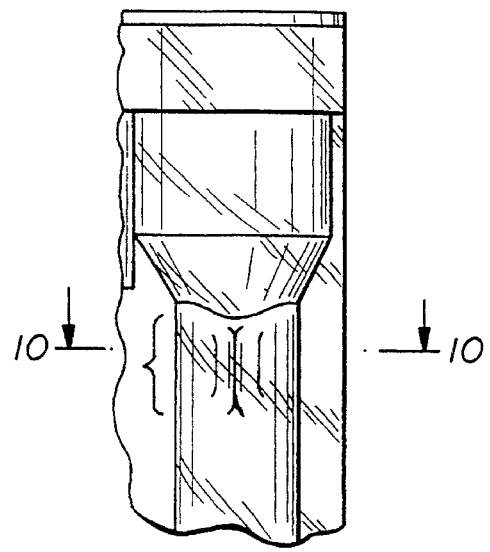
FIG. 9 shows a reaction and separation vessel which has been crimped just below the upper chamber.
Figure 10:
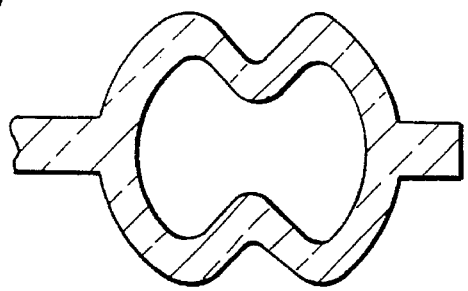
FIG. 10 is a cross-sectional view along line 10—10 of FIG. 9.

Another means by which the orifice between the reaction chamber and the separation chamber below can be diminished is by "crimping" the cassette. This can be achieved by impact extrusion in which the neck of the cassette just beneath the reaction chamber is impacted. The force and duration of the impact determines the degree to which the opening is diminished. The shape of the impacting tool determines the form of the opening. Several configurations are possible. The crimping process can be accomplished in the production line after the columns have been loaded with reagents and glass beads. 816 columns from the manufacturing line were crimped, as described above in order in constrict the opening between the reaction chamber and the separation matrix. The crimp resulted in the cross-sectional shape shown in FIG. 10, through the region indicated by a bracket in FIG. 9. These, along with 768 uncrimped controls were packaged and shipped to and from California as previously described. The reduction of splashes into the reaction chambers caused by the shipping conditions is given in Table 8.

TABLE 8

|  | Number of Tests | Number of Chambers with Splashes | Percentage of Chambers with Splashes |
| --- | --- | --- | --- |
| Columns with Crimps | 816 | 548 | 67% |
| Columns with No Crimps | 768 | 571 | 74% |

What is claimed is:

1. A vessel for conducting an agglutination assay comprising:
    a) an upper chamber having an opening for accepting fluid reactants;
    b) a lower chamber disposed to receive fluid from the upper chamber and containing a matrix for separating agglutinates; and
    c) a barrier separating the upper chamber from the lower chamber and having means for retaining fluid in the upper chamber under normal gravity and atmospheric conditions, while permitting passage of the fluid from the upper chamber to the lower chamber under pressure greater than atmospheric pressure.

2. A vessel of claim 1 wherein said barrier comprises an aperture which has a diameter small enough to retain fluid in the upper chamber under normal gravity and atmospheric pressure.

3. The vessel of claim 2 wherein the diameter of the aperture is in the range of about 0.010 to 0.050 inch.

4. The vessel of claim 3, wherein the diameter of the aperture is 0.020 inch.

5. A vessel for conducting an agglutination assay comprising:
   a) an upper reaction chamber having an opening for receiving fluid reagents and an aperture small enough to retain fluid against normal gravity and atmospheric pressure; and
   b) a lower chamber which communicates with the upper chamber through the aperture, and which contains a separation matrix for separating agglutinates.

6. A vessel according to claim 5 wherein the aperture has a diameter within the range of 0.010 to 0.050 inch.

7. A vessel for conducting an agglutination assay comprising:
   a) a first chamber for receiving and retaining fluid sample and reagents;
   b) a second chamber communicating with the first chamber for receiving fluid from the first chamber, and which contains a separation matrix for separating agglutinates; and
   c) a barrier separating said first and second chambers capable of preventing fluid passage from the first to the second chamber under normal gravity or atmospheric pressure, while allowing fluid passage from the first to second chamber under pressure greater than atmospheric pressure.

8. A vessel according to claim 7 wherein the barrier comprises an aperture of diameter small enough to retain fluids in the first chamber under normal gravity and atmospheric pressure.

9. A vessel according to claim 8 wherein the diameter of the aperture is in the range of from about 0.010 to 0.050 inch.

10. A vessel according to claim 9 wherein the diameter of the aperture is 0.020 inch.

11. A vessel according to claim 8 wherein the aperture comprises a crimp.

* * * * *